United States Patent [19]

McEntire et al.

[11] 4,405,601

[45] Sep. 20, 1983

[54] EXTRACTION AND PURIFICATION OF BIOLOGICALLY ACTIVE LYMPHOKINES

[75] Inventors: John E. McEntire; Ben W. Papermaster, both of Columbia, Mo.

[73] Assignee: Cancer Research Center, Columbia, Mo.

[21] Appl. No.: 265,956

[22] Filed: May 21, 1981

[51] Int. Cl.$^3$ ...................... A61K 35/12; A01N 63/02
[52] U.S. Cl. ..................................................... 424/95
[58] Field of Search ......................................... 424/95

[56] References Cited

PUBLICATIONS

"Nature", vol. 224, Oct. 4, 1969, pp. 38–42, Article by Dumonde et al.

Primary Examiner—Elbert L. Roberts
Attorney, Agent, or Firm—Senniger, Powers, Leavitt and Roedel

[57] ABSTRACT

A biologically active lymphokine fraction which exhibits macrophage activation activity and lymphotoxin activity is prepared from large scale supernatant culture fluids of human lymphoblastoid cultured cell lines grown in the presence of human serum to minimize antigenicity. Growth of lymphoblastoid cells from human lymphoblastoid cultured cell lines is effected and the supernatant culture fluids are harvested, concentrated and clarified. The supernatant culture fluids are then extracted with trichloroacetic acid, guanidine hydrochloride, sodium dodecyl sulfate or perchloric acid as the extracting solvent followed by removal of the solvent. Further purification of the lymphokine fraction can be achieved by treatment with guanidine hydrochloride or sodium dodecyl sulfate as a dissociating solvent and by subjecting the lymphokine fraction to gel filtration, sodium dodecyl sulfate gel electrophoresis and/or high pressure liquid chromatography.

25 Claims, No Drawings

EXTRACTION AND PURIFICATION OF BIOLOGICALLY ACTIVE LYMPHOKINES

The invention described herein was made in the course of work under a grant or award from the Department of Health, Education and Welfare.

BACKGROUND OF THE INVENTION

This invention relates to biologically active materials and the preparation thereof and, more particularly, to biologically active lymphokines and the preparation thereof from human lymphoblastoid cell line sources.

It has been shown that lymphokine-containing fractions obtained from guinea pigs exhibit many of the biological activities associated with lymphokines (D. C. Dumonde et al., Nature, 224, 38, (1969)). It has also been shown that lymphokine-containing fractions or unpurified supernatant preparations exhibit the additional capability of inducing tumor regression in vivo in man and animals (I. D. Bernstein et al., Science, 172, 729 (1971); S. B. Salvin et al., J. Natl. Cancer Inst., 55, 1233, (1975); B. W. Papermaster et al., Res. Commun. Chem. Pathol. Biol., 8, 413 (1974); B. W. Papermaster et al., Clin. Immunol. Immunopathol., 5, 31, (1975); B. W. Papermaster et al., Cancer, 45,1248, (1980); A. S. Hamblin et al., Dev. Biol. Stand., 38, 353, (1978)).

Lymphokines have been recognized since 1964 (see studies of B. R. Bloom and B. Bennet, Science, 153, 80, (1966) and J. R. David, J. Biol. Chem., 56, 72,. (1966)). The term "lymphokine" was coined by D. C. Dumonde et al. (Nature, 224, 38, (1969)). The work in the field to date has been summarized in recent international reviews and symposia (D. C. Dumonde et al., Nature, 224, 38, (1969); S. Cohen et al., Cell. Immunol., 33, 233–244, (1977); A. L. De Weck (Ed.), Biochemical Characterization of Lymphokines, Academic Press, (1980)). B. W. Papermaster et al. (Clin. Immunol. Immunopathol., 5, 31, (1976)) have described the direct effects of locally injected supernatant preparations from the human lymphoblastoid cell line, RPMI 1788, which induced histologically verified regressions in metastatic cutaneous tumor lesions. These studies were confirmed in the United Kingdom by A. S. Hamblin et al. (Dev. Biol. Stand., 38, 353, (1978) who used similar preparations for local and systemic treatment. Studies on lymphokine-induced tumor regression in the mouse have been described by S. B. Salvin et al. (J. Natl. Cancer Inst., 55, 1233, (1975)) and B. W. Papermaster et al. (Clin. Immunol. Immunopathol. 5, 31, (1976)), and the use of a lymphokine preparation in cancer patients for inflammatory skin test reactions has been described by A. Rios et al. (Cancer, 44, 1615, (1979)). Recently, L. B. Schook et al. (Biochemical Characterization of Lymphokines, A. L. De Weck (Ed.), Academic Press, (1980), p. 67) have enumerated a list of human lymphoblastoid cell lines active in lymphokine production.

Partial purification of lymphokine activities, including the Migration Inhibitory Factor (MIF) has been reported by H. G. Remold, J. Immunol., 122, 1920, (1979), lymphotoxin by M. Gately et al., Cell. Immunol., 27, 82, (1976), and others recently summarized in A. L. De Weck (Ed.), Biochemical Characterization of Lymphokines, Academic Press, (1980). Association of lymphokines with albumin and alpha-2 macroglobulin in human serum has been reported by M. C. McDaniel et al., J. Immunol. Meth., 20, 225, (1978); M. E. Smith et al., J. Immunol. Meth., 14, 243,, (1977); J. E. McEntire et al., J. Immunol. Meth., 24, 39, (1978).

It is believed that a major deficiency of the prior art is a lack of appreciation for the binding properties of active lymphokine moieties to protein carriers such as albumin and alpha-2 macroglobulin, with the attendant failure to use stringent extraction and dissociating solvents in order to obtain purified lymphokines free of carrier protein. It is also believed that another problem in the prior art is a deficiency in simple extraction procedures capable of being used with large quantities (100–1000 liters) of cell culture fluid and which do not require additional cumbersome steps to recover the extracted fractions. As a result, previous methods were capable of only producing small quantities of lymphokine preparations for laboratory use in animals or in in vitro assays, but insufficient for sustained clinical trials or biochemical characterization.

There has remained, therefore, an unfulfilled need for a more effective method for producing lymphokine fractions of a higher degree of purity and in larger quantities.

SUMMARY OF THE INVENTION

Among the several objects of the invention may be noted the provision of an improved method for the extraction and purification of biologically active lymphokines from large scale culture supernatants; the provision of such a method which permits the harvesting of lymphokine fractions of high degrees of purity in large quantities; the provision of a method of the type described which affords the production of lymphokine fractions which are non-toxic and active in promoting tumor regression and increasing systemic immunocompetence in mammals; and the provision of such a method which is capable of reproducibility and which may be conveniently carried out to produce lymphokine fractions in large quantities. Other objects and features will be in part apparent and in part pointed out hereinafter.

Briefly, the present invention is directed to an improvement in a method for the extraction and purification of biologically active lymphokines from large scale culture supernatants involving the steps of effecting the growth of lymphoblastoid cells from human lymphoblastoid cultured cell lines and thereafter harvesting, concentrating and clarifying the resulting supernatant culture fluids, the improvement comprising extracting the supernatant culture fluids with a solvent selected from the group consisting of trichloroacetic acid, guanidine hydrochloride, sodium dodecyl sulfate and perchloric acid and removing the solvent to produce a lymphokine fraction which exhibits the capability of inducing cell-mediated immunity reactions and tumor regression in mammals. The invention is also directed to a biologically active lymphokine fraction which exhibits macrophage activation activity and lymphotoxin activity and which is made according to the novel method of the present invention. The invention is further directed to the method of inducing cell-mediated immunity reactions and tumor regression in mammals comprising administering thereto a lymphokine fraction produced by the novel method of the invention.

DESCRIPTION OF THE PREFERRED EMBODIMENT

In accordance with the present invention, we have now found that a more highly purified, non-toxic extract of lymphoblastoid cell line culture fluid having many favorable immunostimulant properties for treatment of cellulose immune deficiency conditions may be produced by an improved method which essentially involves utilizing trichloroacetic acid, guanidine hydrochloride, sodium dodecyl sulfate or perchloric acid as a solvent for extracting supernatant culture fluids prepared by effecting the growth of lymphoblastoid cells from human lymphoblastoic cultured cell lines and thereafter harvesting, concentrating and clarifying the resulting supernatant culture fluids. In the practice of the invention, the use of trichloroacetic acid as the extracting solvent is highly preferred from the standpoint of a large scale preparative method. However, the other aforementioned solvents, even though less preferred, are useful to produce biologically active lymphokine fractions of improved purity. And, as discussed hereinafter, guanidine hydrochloride and sodium dodecyl sulfate are particularly useful as dissociating solvents for further purifying the lymphokine fraction obtained from the main method of the invention.

After the principal solvent extraction step, preferably carried out with trichloroacetic acid as mentioned, the solvent is removed as, for example, by means of gel filtration or by other means known to the art. In general, the lymphokine fraction obtained from the novel solvent extraction method of the invention may be subjected to further purification by gel filtration, sodium dodecyl sulfate gel electrophoresis and/or high pressure liquid chromatography procedures as desired.

Through the practice of the present invention, there is permitted for the first time insofar as is known the harvesting and isolation of lymphokine fractions of high degrees of purity in large quantity into a soluble acid phase. It is believed that this solvent extraction step effects removal of substantially all of the contaminating protein. The resulting acid-extracted fraction is nontoxic and active in promoting tumor regression and in increasing systemic immunocompetence in mammals. While the precise mechanism is not wholly understood, it appears that the method of the invention is effective through disruption of the hydrophobic and electrostatic bonds between lymphokine molecules and carrier proteins as well as preferentially extracting the polar lymphokine molecules into the acid-aqueous phase. In any event, a primary benefit of the present invention is a large scale separation in a single solvent extraction in which the desired precipitate can be removed by filtration or centrifugation and the solvent removed by gel filtration or evaporation. The resulting purified lymphokine fraction may be provided for clinical use without further purification or, as indicated, may be subjected to further purification or separation to provide a lymphokine moiety of a higher degree of purity and homogeneity.

The cell or plasma sources which produce or contain lymphokines are, for example, peripheral blood lymphocytes purified by the method of J. Boyum, Scand. J. Clin. Lab. Invest., 97, 77, (1968), stimulated in culture by lectins or antigens, plasma from patients with various reactive immune conditions such as tuberculosis, or antigenic stimulation such as BCG (Bacillus Calmette Guerin) vaccination (attenuated tuberculosis strain). The lymphoblastoid cells from human lymphoblastoid cultured cell lines described by B. W. Papermaster et al., Clin. Immunol. Immunopathol., 5, 31, (1976) and L. B. Schook et al., Biochemical Characterization of Lymphokines, A. L. De Weck (Ed), Academic Press, (1980), p. 67, are the preferred and presently available practical large scale sources of starting material for use in the practice of the invention. These include, without limitation, the cell lines known as "RPMI 1788," "B-23-3," "B 66," "B 89," "SN 1036," "B-411-4," "B 70," "B 85," "RPMI 8392," "B 76," "BALL-1," "BALM-2," "NALM-6," "B 35-M," "B 46-M," "U-698-M," "MOLT-4F," "RPMI 8402," "HPB-ALL," "K-562," "NALM1," "NALM-16," "Reh" and "NALL-1," all as described and enumerated in Schook et al. supra.

In connection with the present invention, it is important to note the differences between lymphokines and interferons which partially resemble each other in size and properties. Recent evidence on this topic has been cited in A. L. DeWeck (Ed.), Biochemical Characterization of Lymphokines, Academic Press (1980). Interferon has not been detected, for example, in the supernatant fluids of RPMI 1788 or its fractions as shown by A. S. Hamblin et al., Dev. Biol. Stand., 38, 353, (1978), and B. W. Papermaster et al., Clin. Immunol. Immunopathol, 5, 48, (1976).

A generalized description of the practice of the present invention for the preparation of improved lymphokine fractions is as follows:

I. Cell Culture Methods
Cell Maintenance and Storage

A. Preparation of frozen stocks—Stock RPMI 1788 cells (American Type Culture Collection) at a concentration of $1-5 \times 10^6$/ml. were frozen in a medium consisting of 67% RPMI (Flow), 30% fetal calf serum (FCS, Gibco) and 3% dimethylsulfoxide (DMS, Sigma) at pH 7.2. Cell suspensions were equilibrated at room temperature for 30–60 minutes in one milliliter freezing vials. The temperature was subsequently lowered to $-90°$ C. at a rate of 1° C. per minute in a Revco ultra-low freezer. The stocks were routinely rotated every 3–6 months to preserve the viability of the cells.

B. Preparation of maintenance culture—Frozen stocks for initiation of seed cultures were rapidly thawed at 37°–42° C. and transferred to fresh prewarmed (37° C.) RPMI 1640 containing 20% FCS and a mixture of penicillin-streptomycin (Gibco) at a final concentration of 100 i. u. and 100 mcg. per milliliter (complete medium), respectively. DMS was removed by gentle centrifugation and washing $\times 2$ at $100 \times G$ the above medium. After washing, the cells were resuspended to a concentration of $1-2 \times 10^6$ viable cells/ml. in complete medium and incubated at 37° C. The cells were maintained at this concentration for 3–4 days at which time FCS was diminished to 10%. Cell numbers and viability determination were accomplished by hemocytometer counting and trypan blue exclusion.

Generation of Lymphokine Containing Culture Fluids

A. Preparation of human serum—Human plasma, hepatitis antigen negative, was obtained from the Mid-Missouri Red Cross Blood Center. Pooled plasma was brought to 0.02 M in calcium by the addition of appropriate volumes of 40% $CaCl_2$. The plasma was allowed to clot for 3 hours at 30° C. to initiate clot retraction. Serum was harvested after thawing by centrifugation at $2000 \times G$ for 3 hours. Lipid was removed by centrifugation at $125,000 \times G$ for 3 hours in a swinging bucket rotor. Sterilization was effected by filtration through 0.2 micron Nalge filters. All serum was stored at $-35°$ C. until used.

B. Initiation of Culture in Human Serum—Prior to use, the serum was heat-inactivated at 60° C. for 30 minutes. The cells growing vigorously in culture medium supplemented with FCS were transferred to spinner flasks and stirred at the rate of approximately 50-60 rpm. After adaptation to spinner culture (1-3 days), the cells were adapted to human serum containing medium. This was accomplished by alternating centrifugations and washing×2 in excess volumes of RPMI 1640 containing 2% pooled human serum and antibiotics. The cells were suspended after the final wash at a concentration of $1-2 \times 10^6$ viable cells/-ml. in RPMI 1640 plus 2% human serum and no antibiotics for generation of lymphokine-containing supernatants.

C. Generation of Lymphokine-Containing Culture Supernatants—The cells were cultured for 24 hours in a medium consisting of 98RPMI 1640 and 2% pooled human serum, at the stationary phase growth, in spinner flasks with stirring at 50-60 rpm. Concentrations for best yield are between $1-2\times 10^6$ per ml. The supernatants were further clarified by centrifugation at 18,000×G and stored at $-20°$ C. until further processed. The sterility of cultures was tested daily by incubation of culture fluids in thioglycollate broth.

II. Processing of Supernatant Culture Fluids

A. Supernatant Concentration and Desalting—The clarified supernatant was concentrated from 20 liters to about 1 liter over PM-10 membranes in a TCE-5 ultrafiltration device (Amicon Corp., Lexington, Mass.). The concentrate was layered onto a 10×100 cm. column of Sephadex G-25 (Pharmacia, Upsala, Sweden) which had been equilibrated with a volatile buffer, 0.05 M ammonium bicarbonate. The column was eluted with the same buffer and the void volume collected. The desalted protein was frozen and lyophilized in trays on an FTS20-54VP freezer dryer.

B. Ultracentrifugation and Vialing—The powered protein was resuspended in pyrogen-free sterile saline at 20 mg. dry weight/ml. with slow stirring. The solution was centrifuged at 37,000×G for 30 minutes in a Beckman J2-21 equipped with a JA-17 rotor. After this initial clarification, the solution was ultracentrifuged at 144,000×G for 3 hours in a L5-75 preparative ultracentrifuge equipped with a 70Ti rotor (Beckman Instruments, Palo Alto, Calif.). After centrifugation, the material was filtered twice through 0.2 Nalgene filters and the bulk material tested for sterility, endotoxin and mycoplasma as described below. Sterile material was dispended into 5 ml. vials (Wheaton); the vialed lymphokines were lyophilized and stoppered under vacuum in an FTS model 20-54VP freezer dryer.

C. General Compatibility Testing—After resuspension in sterile, injectable water at protein concentrations of 10-20 mg./ml. or higher, the pH and conductivity of the lymphokine solution are tested for compatibility as to salt content by a pH meter and a conductivity meter. Protein concentration was determined by the fluorescamine method of P. Bohlen et al., Arch. Biochem. Biophys., 155, 213, (1973), or, alternatively, by the method of O. H. Lowry et al., J. Biol. Chem. 193,265, (1951).

III. Purification of Lymphokines

To the clarified, crude, resuspended, supernatant solution from above which is physiological (0.15 M) with respect to saline content was slowly added solid trichloroacetic acid to a final concentration of 10% w/v with continuous stirring at 5° C. up to room temperature. The concentration of the trichloroacetic acid may vary, but preferably ranges between approximately 5% and 20% w/v. After 5 to 20 minutes, the precipitate was removed by centrifugation at 37,000×G for 30 minutes.

The supernatant was desalted over a G-25 column equilibrated with 0.05 molar ammonium bicarbonate. The thus eluted protein was pooled, lyophilized and vialed as above and contains lymphokine activity.

As stated, in lieu of trichloroacetic acid as the extracting solvent, perchloric acid (e.g. 10% w/v), guanidine hydrochloride (e.g. 6 molar) or sodium dodecyl sulfate (e.g. 1% w/v) may be employed but give less satisfactory results than trichloroacetic acid from a large scale preparative standpoint. Thus, the use of perchloric acid does not provide comparable yields of the biologically active lymphokine preparation and guanidine hydrochloride and sodium dodecyl sulfate require somewhat extensive desalting and/or removal measures. Also, sodium dodecyl sulfate is not substantially completely removable from the final product. However, guanidine hydrochloride and sodium dodecyl sulfate usefully function as peptide to protein dissociating solvents for further purification of the biologically active lymphokine fraction or extract produced as described above.

Further purification of the biologically active lymphokine fraction may also be achieved, in accordance with the present invention, by gel filtration, or by sodium dodecyl sulfate gel electrophoresis, or by high pressure liquid chromatography or by a combination of these procedures.

The biologically active lymphokine fraction or extract produced by the method of the present invention is active at concentrations of 10-50 μg in vitro in assays for lymphotoxin and macrophage activation, and in vivo in inducing intradermal inflammation in the guinea pig. It is active at concentrations of 0.3-50 nanograms acting in vivo to induce mouse spleen killer cells active against tumor cells in vitro. The lymphokine preparations or fractions of the present invention are approximately 60-250 fold more active than the crude starting material in acting as an adjuvant to chemotherapy of the mouse L1210 tumor by increasing survival and cure rate in tumor bearing animals. The preparations also promote neutrophil and macrophage phagocytosis in vitro.

As indicated, the lymphokine preparations or fractions of the present invention may be utilized alone or as an adjuvant to chemotherapy with a chemotherapeutic agent such as 1-(2-chloroethyl)-3-(4-methylcyclohexyl)-1-nitrosourea (MeCCNU).

Administration of biologically active lymphokine preparations of the invention may be by various modes such as intradermally, subcutaneously and intravenously.

The following examples further illustrate the practice of the invention.

EXAMPLE 1 a. Sixty liters of supernatant fluid were collected from spinner cultures in stationary phase of growth and clarified from cells at 200×G. The collected supernatants were clarified at 18,000×G, pooled, and concentrated over Amicon PM-10 filter membranes. The concentrates were desalted on Sephadex G-25 in 0.05 molar ammonium bicarbonate buffer. High-speed centrifugation of the desalted concentrates was carried out at 37,000×G and ultracentrifugation at 144,000×G for 3 hours.

Trichloroacetic acid extraction on the concentrate (at a trichloroacetic acid final concentration of 10% w/v) was carried out as previously described at room temperature on a solution containing 17 mg. protein/ml. The precipitate was removed by centrifugation at 37,000×G for 30 minutes. The remaining acid supernatant was poured over a G-25 column equilibrated with 0.05 molar ammonium bicarbonate buffer and lyophilized in 1 ml. amounts in sterile vials.

Lymphokine biological activity was measured in serial dilutions of 1 ml. starting volumes (253 micrograms of protein per vial). Lymphotoxin was measured according to the technique of M. E. Smith et al., J. Immunol. Meth., 14,243, (1977). Guinea pig skin inflammatory responses were measured as described by B. W. Papermaster et al., Clin. Immunol. Immunopathol., 5, 48, (1976). Macrophage activiation activity (MAF) was measured according to M. C. McDaniel et al., J. Immunol. Meth., 20, 225, (1978). Natural Killer (NK) cell activity was measured by a method developed by C. D. Gilliland et al., Int. J. Immunopharm 3, 191 (1980), First International Conference on Immunopharmacology (Abstracts). Phagocytosis in human peripheral blood neutrophils was measured according to P. A. Dunn et al., Int. J. Immunopharm., 3, 191 (1980), First International Conference on Immunopharmacology Abstracts. The results are set forth in Table I below:

TABLE I

Lymphokine Biologic Properties of the Starting Material (Crude) and Trichloroacetic Acid Extractable Fraction Compared

| | Assay | Minimal Protein Concentration Required | | Activity Increase in Fraction | Significance |
|---|---|---|---|---|---|
| | | Crude | Fraction | | |
| 1. In Vitro Killer cell (CMC) Induction | Reduction in effector cell ratio | 160 mcg/ml | 2 mcg/ml | 80X | p = .007 |
| 2. In Vivo CMC Induction | (as in 1 above) | 1500 mcg/ml | 9 mcg/ml | 167X | p = .005 |
| 3. In Vitro MAF | Lowest concentration producing significant macrophage killing of L1210 targets | 328 mcg/ml | 7 mcg/ml | 47X | p < .001 |
| 4. Lymphotoxin | Lowest concentration producing direct toxicity of 50% in 24 hrs. | 9100 mcg/ml | 73 mcg/ml | 125X | p < .001 |
| 5. Guinea Pig Skin Reaction | Minimal dose producing 1 cm diameter inflammation (78.5 mm$^2$) | 510 mcg in 0.1 ml | 11 mcg in 0.1 ml | 46X | p < .006 |

CMC = cell mediated cytotoxicity b. Mouse tumor assays in DBA/2J mice inoculated with $10^5$ L1210 lymphoma cells were performed according to C. D. Gilliland et al., First International Conference on Immunopharmacology (Abstracts) (Ibid. 3, 191 (1980)). The tests performed involved the use of a medium control (containing some lymphokine), a crude lymphokine, the chemotherapeutic agent 1-(2-chloroethyl)-3-(4-methylcyclohexyl)-1-nitrosurea (MeCCNU), MeCCNU plus the medium control, MeCCNU plus crude lymphokine, MeCCNU plus trichloroacetic acid extracted medium control and MeCCNU plus trichloroacetic acid extracted lymphokine.

The results are shown in Table II below:

TABLE II

Results utilizing trichloroacetic acid extractable fraction of human RPMI 1788 lymphokine treating DBA/2J mice inoculated with $10^5$ L1210 lymphoma cells

| | Total Animals | Median Survival Time | Long Term* Total Survivors Animals/Group |
|---|---|---|---|
| | 70 | | |
| medium control | 10 | 16 | 0/10 |
| crude lymphokine | 10 | 15 | 0/10 |
| MeCCNU (40 mg/kg) | 10 | 24 | 0/10 |
| MeCCNU (40 mg/kg) + medium control | 10 | 25 | 0/10 |
| MeCCNU (40 mg/kg) + crude lymphokine | 10 | 19 | 0/10 |
| MeCCNU (40 mg/kg) + trichloroacetic acid extractable medium control | 10 | 24 | 0/10 |
| MeCCNU (40 mg/kg) + trichloroacetic acid extractable lymphokine | 10 | 23 | 3/10 |

*Long term survivors represent those mice surviving for longer than 60 days after implant of tumor.

The three animals which survived in the group receiving the combination of the chemotherapeutic agent MeCCNU and the biologically active lymphokine preparation of the present invention were rechallenged later with the same tumor line and were found to be refractory to rechallenge. Thus, enhanced survivals and cures were obtained only with the noted combination and the data are indicitive of the findings obtained with the crude, starting material at concentrations in excess of 200 times greater than the trichloroacetic acid extracted lymphokine fraction.

EXAMPLE 2 a. A simpler procedure for rapid large-scale preparative extraction was carried out as follows with 75 liters of supernatant fluid. Cell culture supernatant was clarified of cells at 200×G and at 37,000×G and concentrated on an Amicon PM-10 filter, as in Example 1, and lyophilized. This lyophilized product was resuspended in 0.15 molar NaCl to 40 mg./ml., stirred for 1 hour at 4° C., and centrifuged at 19,000×G for 30 minutes. Trichloroacetic acid was added as in Example 1 at 2° C. for 30 minutes and the resulting slurry centrifuged at 19,000×G. The supernatant was neutralized with 5 N NaOH to pH 7.0, filtered over a 0.45 micron Nalgene filter, concentrated to 400 ml. on a PM-10 membrane in an Amicon TCF cell, desalted on Sephadex G-25 equilibrated with 0.05 molar ammonium bicarbonate buffer, and lyophilized. The powder was resuspended in distilled water, dispensed into 1 ml. vials and lyophilized.

b. Samples of this preparation were tested for endotoxin as described by J. H. Jorgensen et al., Appl. Microbiol., 26, 43, (1973), and biological activity as in Example 1, and were shown to satisfy the safety standards for clinical investigation according to Federal Register, Vol. 38, No. 223, (1973), pp. 610.11–610.12.

Assay data indicate that the biologically active lymphokine fraction produced by the method of the present invention has increased biologic activity in all assays tested at levels between 60 and 600 times greater than the crude starting materials, depending on the assay, and is clinically active at 60–150 micrograms per dose in inducing local tumor regression. Thus, the invention provides a relatively clean, non-toxic clinically tolerable extract of lymphoblastoid cell line culture fluid which appears to exhibit favorable immunostimulant properties for treatment of cellular immune deficiency conditions.

In view of the above, it will be seen that the several objects of the invention are achieved and other advantageous results attained.

As various changes could be made in the above products and methods without departing from the scope of the invention, it is intended that all matter contained in the above description shall be interpreted as illustrative and not in a limiting sense.

What is claimed is:

1. In a method for the extraction and purification of biologically active lymphokines from large scale culture supernatants comprising the steps of effecting the growth of lymphoblastoid cells from human lymphoblastoid cultured cell lines, and thereafter harvesting, concentrating and clarifying the resulting supernatant culture fluids, the improvement which comprises extracting said supernatant culture fluids with a solvent selected from the group consisting of trichloroacetic acid, guanidine hydrochloride, sodium dodecyl sulfate and perchloric acid and removing said solvent to produce a lymphokine fraction which exhibits the capability of inducing cell-mediated immunity reactions and tumor regression in mammals.

2. The method as set forth in claim 1 wherein said lymphokine fraction is further purified by treatment with a dissociating solvent selected from the group consisting of guanidine hydrochloride and sodium dodecyl sulfate.

3. The method as set forth in claim 1 wherein said solvent is removed by gel filtration.

4. The method as set forth in claim 1 wherein said lymphokine fraction is subjected to further purification by a procedure selected from the group consisting of gel filtration, sodium dodecyl sulfate gel electrophoresis and high pressure liquid chromatography.

5. The method as set forth in claim 1 wherein the concentration of trichloroacetic acid is approximately 10% w/v.

6. The method as set forth in claim 2 wherein said dissociating solvent is 6 molar guanidine hydrochloride.

7. The method as set forth in claim 2 wherein said dissociating solvent is a 1% sodium dodecyl sulfate solution.

8. The method of producing lymphokine fraction which exhibits the capability of inducing cell-mediated immunity reactions and tumor regression in mammals by the extraction and purification of biologically active lymphokines from large scale culture supernatants comprising the steps of effecting the growth of lymphoblastoid cells from human lymphoblastoid cultured cell lines, harvesting, concentrating and clarifying the resulting supernatant culture fluids, extracting said supernatant fluids with a solvent selected from the group consisting of trichloroacetic acid, guanidine hydrochloride, sodium dodecyl sulfate and perchloric acid, and removing said solvent.

9. The method as set forth in claim 8 wherein said lymphokine fraction is further purified by treatment with a dissociating solvent selected from the group consisting of guanidine hydrochloride and sodium dodecyl sulfate.

10. The method as set forth in claim 8 wherein said solvent is removed by gel filtration.

11. The method as set forth in claim 8 wherein said lymphokine fraction is subjected to further purification by a procedure selected from the group consisting of gel filtration, sodium dodecyl sulfate gel electrophoresis and high pressure liquid chromatography.

12. The method as set forth in claim 8 wherein the concentration of trichloroacetic acid is approximately 10% w/v.

13. The method as set forth in claim 9 wherein said dissociating solvent is 6 molar guanidine hydrochloride.

14. The method as set forth in claim 9 wherein said dissociating solvent is a 1% sodium dodecyl sulfate solution.

15. The method of inducing cell-mediated immunity reactions and tumor regression in mammals comprising administering thereto a lymphokine fraction produced by effecting the growth of lymphoblastoid cells from human lymphoblastoid cultured cell lines, harvesting, concentrating and clarifying the resulting supernatant culture fluids, extracting aid supernatant culture fluids with a solvent selected from the group consisting of trichloroacetic acid, guanidine hydrochloride, sodium dodecyl sulfate and perchloric acid, and removing said solvent.

16. The method as set forth in claim 15 wherein said lymphokine fraction has been further purified by treatment with a dissociating solvent selected from the group consisting of guanidine hydrochloride and sodium dodecyl sulfate.

17. The method as set forth in claim 15 wherein said solvent is removed by gel filtration.

18. The method as set forth in claim 15 wherein said lymphokine fraction has been subjected to further purification by a procedure selected from the group consisting of gel filtration, sodium dodecyl sulfate gel electrophoresis and high pressure liquid chromatography.

19. The method as set forth in claim 15 wherein the concentration of trichloroacetic acid is approximately 10% w/v.

20. The method as set forth in claim 16 wherein said dissociating solvent is 6 molar guanidine hydrochloride.

21. The method as set forth in claim 16 wherein said dissociating solvent is a 1% sodium dodecyl sulfate solution.

22. The method as set forth in claim 15 wherein said lymphokine fraction is administered intravenously.

23. The method as set forth in claim 15 wherein said lymphokine fraction is administered intradermally.

24. The method as set forth in claim 15 wherein said lymphokine fraction is administered subcutaneously.

25. The method as set forth in claim 15 wherein said lymphokine fraction is administered as an adjuvant to chemotherapy.

* * * * *